United States Patent [19]

Mrozik

[11] 4,005,199

[45] Jan. 25, 1977

[54] SUBSTITUTED BENZENESULFONAMIDES AS ANTHELMINTICS

[75] Inventor: Helmut H. Mrozik, Matawan, N.J.

[73]* Assignee: Merck & Co., Inc., Rahway, N.J.

[22] Filed: Oct. 6, 1975

[21] Appl. No.: 619,981

Related U.S. Application Data

[60] Continuation of Ser. No. 541,540, Jan. 16, 1975, abandoned, which is a division of Ser. No. 472,002, May 22, 1974, which is a division of Ser. No. 326,652, Jan. 26, 1973, abandoned, which is a continuation of Ser. No. 135,433, April 19, 1971, abandoned.

[52] U.S. Cl. .............................................. 424/228
[51] Int. Cl.$^2$ ........................................ A61K 31/63
[58] Field of Search ..................................... 424/228

[56] References Cited

OTHER PUBLICATIONS

Chemical Abstracts 60:6770i (1964).

*Primary Examiner*—Jerome D. Goldberg
*Attorney, Agent, or Firm*—David L. Rose; J. Jerome Behan

[57] ABSTRACT

This invention relates to a novel method for the treatment of parasitic diseases and the compositions used in said treatment. More specifically this invention relates to benzenesulfonamides substituted at the 3, 4, and 5 positions of the benzene ring and to the use of such compounds for the treatment of mature and immature liver fluke infections.

6 Claims, No Drawings

SUBSTITUTED BENZENESULFONAMIDES AS ANTHELMINTICS

This is a continuation of application Ser. No. 541,540 now abandoned filed Jan. 16, 1975 which is a divisional of Ser. No. 472,002 filed May 22, 1974 which is a divisional of Ser. No. 326,652 now abandoned filed Jan. 26, 1973 which is a continuation of Ser. No. 135,433 filed Apr. 19, 1971 now abandoned.

SUMMARY OF THE INVENTION

This invention is concerned with a novel method for the treatment of liver fluke infection due to either mature and immature fluke. More particularly it is concerned with the use of benzenesulfonamide compounds variously substituted at the 3, 4, and 5 positions to effect this treatment. This invention is also concerned with compositions containing said benzenesulfonamides for administration to animals infected with mature or immature liver fluke. Said compositions may also contain other active ingredients such as known anthelmintics or fasciolicides. Further aspects of this invention will become apparent on reading the following description.

DESCRIPTION OF THE PRIOR ART

Sulfonamides in general as well as benzenesulfonamide compounds have been known and synthesized in the art for many years. They have generally been prepared and studied for their activity as antibacterial and diuretic agents and much data is published concerning the bacteriostatic and diuretic activity of sulfonamide compounds. That sulfonamides would have activity against mature and immature liver fluke was not known heretofore.

DESCRIPTION OF THE INVENTION

The compounds of this invention which are useful for the treatment of mature and immature liver fluke infections are represented by the following structural formula:

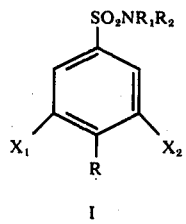

wherein R is hydrogen or amino; $X_1$ and $X_2$ are each halogen, trifluoromethyl or nitro; and $R_1$ and $R_2$ are each hydrogen or loweralkyl.

The term "loweralkyl" in this description means alkyl radicals containing from 1 to 5 carbon atoms, either straight or branched chain. Exemplary are the groups methyl, ethyl, propyl, butyl, amyl, isoamyl, isopropyl, tert-butyl, and the like.

When reference is made to "halo" or "halogen" the term includes fluorine, chlorine, bromine and iodine.

PREFERRED EMBODIMENTS OF THE INVENTION

The preferred embodiments of the instant invention are represented by formula I where $X_1$ and $X_2$ are halogen and in particular when $X_1$ and $X_2$ are bromine.

Compounds exemplary of the preferred embodiments of the invention are:
 4-amino-3,5-dibromobenzenesulfonamide,
 4-amino-3,5-dibromo-N-methylbenezenesulfonamide,
 4-amino-3,5-dichloro-N-ethylbenzenesulfonamide,
 3,5-dibromobenzenesulfonamide,
 3,5-dibromo-N-methylbenzenesulfonamide,
 3,5-dibromo-N-ethylbenzenesulfonamide, and
 3,5-dichloro-N,N-dimethylbenzenesulfonamide.

While many compounds described by formula I are known in the art, some are unique and have not been described heretofore in the art. It is another object of this invention to provide novel compounds within the definition of formula I, which are active as anthelmintic agents and specifically as fasciolicides. Such novel compounds are provided when one or both of $X_1$ and $X_2$ are trifluoromethyl and when $X_1$ is a halogen and $X_2$ is a nitro group. R, $R_1$, and $R_2$ are as defined previously. These novel compounds are exemplified by the following:
 3,5-bis-trifluoromethylbenzenesulfonamide,
 4-amino-3,5-bis-trifluoromethylbenzenesulfonamide,
 3-bromo-5-trifluoromethylbenzenesulfonamide,
 4-amino-3-nitro-5-trifluoromethylbenzenesulfonamide,
 3,5-bis-trifluoromethyl-N-methylbenzenesulfonamide,
 4-amino-3-bromo-5-trifluoromethyl-N-isopropylbenzenesulfonamide,
 4-amino-3-chloro-5-trifluoromethylbenzenesulfonamide,
 4-amino-3-bromo-5-nitrobenzenesulfonamide,
 3-bromo-5-nitrobenzenesulfonamide, and
 4-amino-3-chloro-5-nitro-N-methylbenzenesulfonamide.

The compounds of the present invention have utility in the field of animal therapy. They are effective anthelmintics and are especially effective against both mature and immature liver fluke of the species *Fasciola gigantica* and *Fasciola hepatica*, the common liver fluke in sheep and cattle. The preferred dosage levels depend on the type of compound to be employed, the type of animal to be treated, the particular helminth to be combatted, and the severity of the helminthic infestation. In general, effective fluke eradication is achieved when the compounds are administered orally at dosage levels of from about 1 to 300 mg/kg of animal body weight and preferably from about 10 to 100 mg/kg of animal body weight. The compounds of the present invention may be administered in a variety of ways depending upon the particular animal employed, the type of anthelmintic treatment normally given to such animal, the materials employed and the particular helminths being combatted. It is preferred to administer them in anthelmintically effective amounts in a unit oral or parenteral, most preferably oral, dose at a time when fluke infection is apparent or suspected in the animal.

In addition to the inactive ingredients in the composition, said composition may contain one or more other active ingredients which may be selected from the compounds described by formula I or from other known anthelmintic agents. Beneficial results are obtained when the compounds of formula I are combined with an anthelmintic agent such as thiabendazole (2-(4-thiazolyl)benzimidazole), tetramisole (di-2,3,5,6-tetrahydro-6-phenylimidazo[2,1-b]thiazole), Rafoxanide (3,5-diiodo-3'-chloro-4'-(p-chlorophenoxy)salicylanilide), Parbendazole (5-n-butylbenzimidazo-2-methylcarbamate, and phenothiazine, known anthelmintic agents.

In general, compositions containing the active anthelmintic compound are employed. The amounts of the anthelmintic ingredient in the composition as well as the remaining constituents vary according to the type of treatment to be employed, the host animal and the particular helmintic infestation being treated. In general, however, compositions suitable for oral administration, containing a total weight percent of the active compound or compounds ranging from 0.01 to 95% will be suitable with the remainder of the compositions being any suitable carrier or vehicle. A number of modes of treatment may be employed and each to some extent determines the general nature of the composition. For example, the anthelmintic compounds may be administered to domesticated animals in a unit oral dosage form such as a tablet, bolus, capsule, or drench; a liquid oil base form suitable for parenteral administration or they may be compounded as a feed premix to be later admixed with the animals feedstuff. When the compositions are to be solid unit dosage forms as in tablets, capsules or boluses, the ingredients other than the active compounds may be any other non-toxic vehicle convenient in the preparation of such forms and preferably materials nutritionally suitable such as starch, lactose, talc, magnesium stearate, vegetable gums and the like. Moreover, when capsules are employed, the active compound may be used in essentially undiluted form, the only extraneous material being that of the capsule casing itself which may be hard or soft gelatin or any other acceptable encapsulating material. When the dosage form is to be used for parenteral administration the active material is suitably admixed with an acceptable oil base vehicle preferably of the vegetable oil variety such as peanut oil, cotton seed oil and the like. In all such forms, that is, in tablets, boluses, capsules and oil base formulations, the active compound conveniently ranges from about 5 to 80% by weight of the total composition.

When the compounds are used in the form of a drench, the anthelmintic agents may be mixed with or adsorbed on agents which will aid in the subsequent suspending of the active compounds in water such as bentonite, clays, silica, water soluble starches, cellulose derivatives, gums, surface active agents and the like to form a dry pre-drench composition, and this pre-drench composition is added to water just before use. In the pre-drench formulation, in addition to the suspending agent, such ingredients as preservatives, antifoam compounds or other suitable diluents or solvents may be employed. Such a dry product may contain as much as 95% by weight of the active compound, the rest being excipient. Preferably, the solid composition contains from 30 to 95% by weight of the active compound. Enough water should be added to the solid product to provide the proper dosage level with a convenient amount of liquid for a single oral dose. The commonly used measure in the field is 1 fluid ounce of material and thus 1 fluid ounce of a drench should contain enough of the anthelmintic compound to provide an effective dosage level. Liquid drench formulations containing from 10 to 50% by weight of dry ingredients will in general be suitable with a preferred range being from 15 to 25 weight percent.

When the compositions are intended to be used in feeds, feed supplements or feed premixes, they will be mixed with suitable ingredients of the animals nutrient ration. Solid orally ingestible carriers normally used for such purposes such as distillers dried grains, corn meal, citrus meal, fermentation residues, ground oyster shells, citrus meal, fermentation residues, attapulgus clay, wheat shorts, molasses solubles, corn cob meal, vegetable substances, toasted dehulled soya flour, soya bean meal feed, antibiotic mycellia, soya grits, crushed limestone and the like are all suitable. The active compounds are intimately dispersed or admixed throughout the active solid carrier by methods such as grinding, melting, or tumbling. By selecting a proper diluent and by altering the ratio of carrier to active ingredient, compositions of any desired concentration may be prepared. Feed supplement formulations containing from about 10 to 30% of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration desired for controlling or treating the helminth infection by way of animal ration. Although the preferred level in feeds will depend on the particular compounds being employed, the active compounds of this invention are normally fed at levels of 0.01 to 3% by weight. As stated above, animals are preferably treated at a time when the infestation is apparent or suspected and the most preferred method of such treatment is with single oral doses. Thus, administration of medicated feed is not preferred but may be employed. Similarly, the amounts of drug present in the feed may be reduced to levels in the order of 0.01% to 0.5% by weight, based on the weight of the feed and the medicated feed administered over prolonged periods. This could be in the nature of a preventive or prophylactic measure. Another method of administering the compounds of this invention to animals whose feeds are conveniently pelleted such as sheep is to incorporate them directly into the pellets. For instance, the anthelmintic compounds are readily incorporated in the nutritionally adequate alfafa pellets at levels of 2 to 10 g. per pound for therapeutic use and lower levels for prophylactic use, and such pellets fed to the animals.

Examples of compositions suitable for administration to animals are:

A typical bolus composition is as follows:

| | |
|---|---|
| 4-Amino-3,5-dibromobenzenesulfonamide | 6.0 g. |
| Dicalcium phosphate | 1.0 g. |
| Starch | 0.7 g. |
| Guar gum | 0.16 g. |
| Talc | 0.11 g. |
| Magnesium stearate | 0.028 g. |

A typical drench composition is as follows:

| | |
|---|---|
| 3,5-Dibromobenzenesulfonamide | 4.5 g. |
| Benzalkonium chloride | 0.6 ml. |
| Antifoam emulsion | 0.06 g. |
| Hydroxyethyl cellulose | 0.3 g. |
| Sodium phosphate monobasic | 0.3 ml. |
| Water | q.s. to 30 ml. |

Examples of typical feed premix supplements are as follows:

| | |
|---|---|
| A) 4-Amino-3,5-ditrifluoromethylbenzene- | |
| sulfonamide | 10 lbs. |
| Corn meal | 90 lbs. |
| B) 4-Amino-3-bromo-5-nitrobenzene | |
| sulfonamide | 20 lbs. |
| soybean mill feed | 80 lbs. |

The above feed premix supplements are combined with the animals regular feed, intimately mixing therewith such that the final concentration of the active ingredient is from 0.01 to 3% by weight.

The fasciolicidal activity of the compounds of this invention is illustrated by the following biological data in which immature liver fluke infestations in sheep were treated with the representative active compounds. The data was obtained by necropsy following the treatment of infected sheep.

| | Dosage (mg/kg) | Live Flukes | Dead Flukes |
|---|---|---|---|
| 1. 4-Amino-3,5-dibromobenzenesulfonamide | | | |
| | 100 | 0 | 26 |
| | 100 | 0 | 36 |
| | 100 | 0 | 34 |
| 2. 3,5-Dibromobenzenesulfonamide | | | |
| | 100 | 0 | 15 |
| | 100 | 0 | 5 |
| | 100 | 0 | 40 |
| | 50 | 0 | 35 |
| | 50 | 0 | 29 |
| | 50 | 0 | 38 |

The compounds of the instant invention may be prepared by various processes, some of which are known in the art and which generally dulminate with the following reaction:

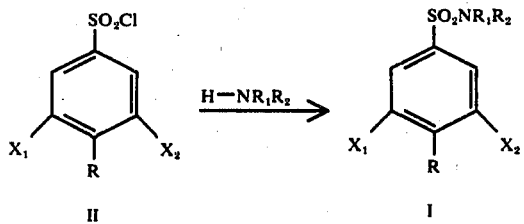

wherein $R$, $R_1$, $R_2$, $X_1$ and $X_2$ are as previously defined. The benzenesulfonyl chloride (II) is converted to the benzenesulfonamide (I) by treatment with ammonia or a primary or secondary amine to afford the unsubstituted, monosubstituted or disubstituted benzenesulfonamide, respectively.

The reaction of the benzenesulfonyl chloride with ammonia is usually effected with liquid ammonia although aqueous solutions of ammonia have proven successful. A large molar excess of from 5 to 50 times of ammonia is used at temperatures below the reflux temperature of liquid ammonia. The temperature of dry ice is preferred. When aqueous ammonia is employed, concentrated solutions are preferred of from 20 to 40% by weight at a temperature of from 0° C. to room temperature. The benzenesulfonamide is isolated by techniques and procedures known to those skilled in the art.

When the benzenesulfonylchloride is treated with a primary or secondary amine the reaction is preferably run in a solvent. Inert solvents may be used which will dissolve both the amine and the benzenesulfonylchloride. Solvents must be chosen, however, that will not react with the sulfonyl chloride. Benzene, methylene chloride, chloroform, tetrahydrofuran, toluene and acetone are examples of satisfactory solvents. During the reaction 1 mole of hydrogen chloride is liberated. It is preferred to add to the reaction medium at least 1 mole of a base which will neutralize the liberated HCl but will not react with the benzenesulfonyl chloride. Tertiary amines such as diethylamine and pyridine are satisfactory. Often the tertiary amine can be used in large excess as the solvent. Another method of effecting the same result is to use a large excess of the primary or secondary amine as the solvent. An alternative process which may be employed comprises the use of an inorganic base such as an alkali metal carbonate or bicarbonate in combination with one of the above listed inert solvents.

In the above reactions which do not employ liquid ammonia, the reaction is run at a temperature of from room temperature to the reflux temperature of the reaction mixture. Where liquid ammonia is the reactant the temperature is the temperature of refluxing liquid ammonia.

The reaction is generally run for a duration of from 1 to 36 hours depending on the temperature employed, the duration of the reaction being inversely proportional to the temperature. In general, the reaction is complete after stirring at room temperature for about 10 hours.

The intermediate benzenesulfonyl chloride compounds may be prepared by several procedures. A benzene compound unsubstituted at the position where the sulfonamide group is desired may be sulfonated using, for example, fuming sulfuric acid to afford the benzenesulfonic acid which may be converted to the benzenesulfonyl chloride with a chlorinating agent such as phosphorous pentachloride. This may also be affected in a single step by treating the above benzene derivative with chlorosulfonic acid.

Aniline derivatives may be used to prepare the desired benzenesulfonylchloride compound by diazotizing the amino group and treating the diazonium salt with cupric chloride and sulfur dioxide. Where the chlorobenzene precursor is available, in which the chloro substituent is activated by a strongly electron withdrawing group such as nitro in the ortho- or parapositions to the chloro substituent, the thiophenol derivative may be prepared therefrom and this converted to the sulfonyl chloride derivative. The thiophenol derivative is thus prepared by treating the chlorobenzene derivative with sodium sulfide, and treating the resultant product with chlorine gas in aqueous acetic acid solution.

In the synthesis of the compounds of formula I it is often necessary to protect certain groups which are susceptable to attack by reagents employed in certain of the synthetic steps hereinabove described. The amino group is sensitive to many reagents and may readily be protected by preparing the acetamido derivative or employing starting materials which have a nitro group present, and subsequently reducing the nitro to the amine. The acetamido derivative is readily prepared from the amine and a carboxylic acid halide or anhydride. The amine can be liberated by acid or base catalyzed hydrolysis. The amine can be prepared from the nitro group by catalytic or chemical reduction.

The following examples are typical of the procedure employed to synthesize the compounds of this invention. The examples are presented so that the invention might be more fully understood and should not be construed as being limitative of the invention.

EXAMPLE 1

4-Amino-3-bromo-5-trifluoromethylbenzenesulfonamide

A. 4-Nitro-3-trifluoromethylbenzenethiol

A stirred solution of sodium sulfide monohydrate 65.4 g. (0.276 moles) in 1 liter of water is treated with 50 g. (0.222 moles) of 4-chloro-2-trifluoromethylnitrobenzene in 500 ml. of acetone over 1½ hour. The reaction mixture is stirred for 14½ hours and the resultant solution treated with 25 ml. of concentrated hydrochloric acid. An oil separates from the reaction mixture which is dissolved in 200 ml. of ether, washed with water and extracted with 2.5 N sodium hydroxide solution. The aqueous solution is washed with ether and acidified with 25 ml. of hydrochloric acid. The resulting oil is extracted with ether and the ether solution washed with water affording 47 g. of 4-nitro-3-trifluoromethylbenzenethiol which is used in the next step.

B. 4-Nitro-3-trifluoromethylbenzenesulfonylchloride

A solution of 47 g. of 4-nitro-3-trifluoromethylbenzenethiol in 100 ml. of glacial acetic acid is added dropwise to 1 liter of saturated chlorine water with continuous stirring at from 0°–10° C. During the addition the concentration of chlorine is maintained by bubbling more chlorine gas into the solution. Stirring is continued for 1½ hours and the gummy solid precipitate filtered, washed with water and dried at room temperature affording 22.3 g. of a gummy solid. The solid material is taken up in methylene chloride and dried over magnesium sulfate, filtered and evaporated affording an oil which is used without purification in subsequent steps.

C. 4-Amino-3-trifluoromethylbenzenesulfonamide 22.3 C. of 4-nitro-3-trifluoromethylbenzenesulfonylchloride is added dropwise with stirring to 125 ml. of liquid ammonia in a dry ice bath. The dry ice bath is removed and the resulting dark solution is stirred, the excess ammonia being allowed to evaporate spontaneously. The residue is treated with water and acetic acid to neutralize the residual ammonia. The solid material thus obtained is washed with water and dried affording 17.8 g. of the crude product. This is recrystallized from toluene using charcoal to afford 10 g. of 4-nitro-3-trifluoromethylbenzenesulfonamide, m.p. 187° to 190° C.

1.0 G. of 4-nitro-3-trifluoromethylbenzenesulfonamide is hydrogenated over 5% Ruthenium on charcoal in 20 ml. of absolute ethanol at room temperature under 40 lbs. of hydrogen for 5 hours. The hydrogen uptake is 100% of theory. The mixture is filtered, evaporated and dried affording 0.87 g. of crude solid. This material is recrystallized from toluene affording 0.75 g. of 4-amino-3-trifluoromethylbenzenesulfonamide, m.p. 150° to 151° C.

D. 4-Amino-3-bromo-5-trifluoromethylbenzenesulfonamide

A suspension of 0.69 g. (0.029 moles) of 3-trifluoromethyl-4-aminobenzenesulfonamide in 7 ml. of water and 7 ml. of 48% hydrobromic acid is treated dropwise with 0.16 ml. of liquid bromine and stirred for 3 hours at room temperature. The reaction mixture is filtered, the solid material washed with 10% aqueous sodium bicarbonate, water and dried. The dried solid is recrystallized from toluene affording 0.76 g. of 4-amino-3-bromo-5-trifluoromethylbenzenesulfonamide m.p. 248°–252° C.

EXAMPLE 2

3,5-Bis-trifluoromethylbenzenesulfonylchloride

A solution of 3,5-bis-trifluoromethylaniline (11.4 g.) 0.05 moles, in 40 ml. of glacial acetic acid is treated at room temperature with 8.1 ml. of concentrated hydrochloric acid. The solution is cooled to from −5° to 0° C. and treated with a solution of 3.50 g. (0.051 moles) of sodium nitrite in 7.0 ml. of water over 10 minutes. The resulting suspension is stirred at 0° C. for 1 hour. This solution is added to a suspension of 50 ml. of glacial acetic acid and 1.0 g. of cupric chloride which is saturated with sulfur dioxide at 0° C. During the addition, gas is evolved from the reaction mixture and when the gas evolution ceases, the reaction mixture is further saturated with sulfur dioxide at room temperature, bubbling the sulfur dioxide into the reaction mixture for approximately 20 minutes. The sulfur dioxide bubbling is stopped and the reaction is stirred at room temperature for 1 hour. The solution is poured onto ice, filtered, and the solid dried affording 12.45 g. of 3,5-bis-trifluoromethylbenzenesulfonylchloride. It is of sufficient purity to be used as is in the next step.

EXAMPLE 3

3,5-Bis-trifluoromethylbenzenesulfonamide

Approximately 60 to 70 ml. of liquid ammonia in a dry ice bath is treated portionwise with stirring with 12.4 g. of 3,5-bis-trifluoromethylbenzenesulfonyl chloride. The resulting dark solution is allowed to evaporate spontaneously with stirring. The residue is placed on a water aspirator to remove any excess ammonia and the reaction mixture is treated with a mixture of water and a small amount of glacial acetic acid. The suspension is filtered and the solid material dried affording 10.09 g. of crude product. The crude product is recrystallized from toluene using charcoal, to give 8.73 g. of 3,5-bis-trifluoromethylbenzenesulfonamide, m.p. 183° to 185° C.

EXAMPLE 4

4-Acetylamino-3,5-bis-trifluoromethylaniline

A. 4-Acetylamino-3,5-bis-trifluoromethylnitrobenzene

A mixture of 8.2 g. of 4-nitro-2,6-bis-trifluoromethylaniline, 3.6 g. acetic anhydride, and 20 ml. of pyridine is heated for 48 hours on a steam bath. The reaction mixture is poured onto ice water and the solid material is filtered, dried and recrystallized from isopropanol affording 4-acetylamino-3,5-bis-trifluoromethylnitrobenzene.

B. 4-Acetylamino-3,5-bis-trifluoromethylaniline

A solution of 7.9 g. of 4-acetylamino-3,5-bis-trifluoromethylnitrobenzene in 200 ml. of ethanol is hydrogenated under 40 lbs. of hydrogen pressure with 1 g. of 5% palladium on charcoal catalyst. When the calculated amount of hydrogen is consumed, the solution is filtered and concentrated in vacuo to give 4-acetylamino-3,5-bis-trifluoromethylaniline.

EXAMPLE 5

4-Amino-3,5-bis-trifluoromethylbenzenesulfonamide 5.7 G. of 4-acetylamino-3,5-bis-trifluoromethylaniline is dissolved in 16 ml. of acetic acid and cooled to 10° C., 3.2 ml. of concentrated hydrochloric acid is added, and the mixture cooled to 0°–5° C. with stirring. A solution of 1.4 g. of sodium nitrite in 4 ml. of water is added dropwise, with vigorous stirring and the resultant mixture stirred for ½ hour. The aqueous diazonium salt solution is then added to a solution of 0.4 g. of cupric chloride in 50 ml. of acetic acid which has been previously saturated at 20° C. with sulfur dioxide. The reaction mixture is stirred for 10 minutes, while sulfur dioxide is bubbled through this mixture and for 20 minutes further. The reaction mixture is poured into ice, extracted with methylene chloride, washed with water, dried and evaporated in vacuo. The residual 4-acetylamino-3,5-bis-trifluoromethylbenzenesulfonylchloride is again dissolved in methylene chloride and added to an excess of liquid ammonia. The contents of the flask is allowed to evaporate at room temperature overnight, affording 4-acetylamino-3,5-bis-trifluoromethylbenzenesulfonamide. This is taken up with 25 ml. of 6N hydrochloric acid and treated on a steam bath for 3 hours. It is cooled in ice and allowed to crystallize. The residue is collected by filtration, washed with water, and crystallized from aqueous ethanol to afford pure 4-amino-3,5-trifluoromethylbenzenesulfonamide.

EXAMPLE 6

4-Amino-3-nitro-5-trifluoromethylbenzenesulfonamide

A. 4-Acetylamino-3-trifluoromethylbenzenesulfonylchloride 2.0 G. of α,α,α-trifluoro-o-acetotoluidide and 5.0 ml. of chlorosulfonic acid is heated on a steam bath for 45 minutes. The reaction mixture is poured slowly into a mixture of ice and water. Then, the aqueous suspension is extracted with methylene chloride, washed with water, dried and concentrated in vacuo affording 2.0 g. of 4-acetylamino-3-trifluoromethylbenzenesulfonylchloride which is used as is for the next step.

B. 4-Acetylamino-3-nitro-5-trifluoromethylbenzenesulfonylchloride 3.0 G. of 4-acetylamino-3-trifluoromethylbenzenesulfonylchloride is dissolved in 15 ml. of concentrated sulfuric acid. 0.9 Moles of nitric acid is added dropwise over a period of 15 minutes, while the temperature is kept below 35° C. When the addition is complete the reaction mixture is stirred at room temperature for 2 hours. The reaction mixture is poured onto 150 ml. of ice water and the precipitate is filtered, washed with water and dried affording 4-acetylamino-3-nitro-5-trifluoromethylbenzenesulfonylchloride, used directly in the next step.

C. 4-Amino-3-nitro-5-trifluoromethylbenzenesulfonamide 1.3 G. of 4-acetylamino-3-nitro-5-trifluoromethylbenzenesulfonylchloride is combined with 13 ml. of concentrated aqueous ammonia and stirred at room temperature for 5 hours. The resultant solution is concentrated to one third of the original volume and the precipitate is allowed to age for 1 hour. The suspension is filtered, washed with water and dried, affording a mixture of 4-acetylamino-3-nitro-5-trifluoromethylbenzenesulfonamide and 4-amino-3-nitro-5-trifluoromethylbenzenesulfonamide. The crude mixture (750 mg.) is heated at reflux with 7.5 ml. of 6N hydrochloric acid for 2 hours. The resultant solution is then cooled in an ice bath, and the resulting precipitate filtered, washed with water, recyrstallized from aqueous ethanol affording pure 4-amino-3-nitro-5-trifluoromethylbenzenesulfonamide.

EXAMPLE 7

4-Amino-3-bromo-5-nitrobenzenesulfonamide

A. 4-Acetylamino-3-nitrobenzenesulfonylchloride 116.8 G. (0.50 moles) of acetylaminobenzenesulfonylchloride is dissolved in 600 ml. of concentrated sulfuric acid and cooled to 5° C. A previously prepared mixture of 45 ml. of concentrated nitric acid and 50 ml. of concentrated sulfuric acid is added dropwise at such a rate that the temperature is maintained at from 3° to 6° C. When the addition is complete stirring is continued for 75 minutes at 5° C. The reaction mixture is poured onto 2.5 liters of ice with caution. The supernatant liquid is decanted and the residual material dissolved in hot benzene, separated from some water, cooled and dried over sodium sulfate. The benzene solution is filtered and the filtrate evaporated to dryness. The residue is triturated with ether and the solid material filtered and used as is in the next step.

B. 4-Acetylamino-3-nitrobenzenesulfonamide 13.1 G. of 4-Acetylamino-3-nitrobenzenesulfonylchloride is suspended in 130 ml. of concentrated ammonium hydroxide and stirred at room temperature for 1½ hours. The reaction mixture is concentrated to ⅓ of the original volume by boiling, cooling and filtering. The solid material is recrystallized from 70% ethanol/water affording 7.5 g. of 4-acetylamino-3-nitrobenzenesulfonamide, m.p. 182°–183° C.

C. 4-Amino-3-nitrobenzenesulfonamide 7.5 G. of 4-acetylamino-3-nitrobenzenesulfonamide is dissolved in 60 ml. of 6N hydrochloric acid and refluxed for 2 hours. The reaction mixture is cooled, filtered, and the solid material washed with water and dried. The dried 4-amino-3-nitrobenzenesulfonamide has a m.p. of 208°–210° C. and is of sufficient purity for use in the next step.

D. 4-Amino-3-bromo-5-nitrobenzenesulfonamide 7.0 G. of 4-amino-3-nitrobenzenesulfonamide is suspended in 150 ml. of methanol at room temperature and brominated with 5.2 g. of liquid bromine added dropwise over 15 minutes. The reaction mixture is filtered and the solid material recrystallized from isopropanol affording 4-amino-3-bromo-5-nitrobenzenesulfonamide, m.p. 216°–218° C.

EXAMPLE 8

3,5-Dibromo-N-isopropylbenzenesulfonamide 3.0 G. of 3,5-dibromobenzenesulfonylchloride is added to a solution of 17.7 g. of isopropylamine in 25 ml. of water at room temperature. A complete solution results which is stirred for 2 hours and poured onto 250 ml. of water. The precipitate is filtered, washed with water, and dried affording 3,5-dibromo-N-isopropylbenzenesulfonamide, m.p. 105° to 107° C.

EXAMPLE 9

4-Amino-3,5-dibromo-N-isopropylbenzenesulfonamide 4.0 G. of 4-amino-3,5-dibromobenzenesulfonyl chloride is added to a solution of 34 ml. of isopropylamine in 30 ml. of water. The resultant solution is stirred overnight at room temperature and poured onto 250 ml. of an ice/water mixture. The precipitate is filtered, washed with water and dried. The dried filtrate is recrystallized from isopropanol affording pure 4-amino-3,5-dibromo-N-isopropylbenzenesulfonamide, m.p. 181° to 183° C.

EXAMPLE 10

4-Amino-3,5-dibromobenzenesulfonylchloride

A solution of 15 g. of 4-amino-3,5-dibromobenzenesulfonamide in 45 ml. of chlorosulfonic acid is heated on a steam bath at 95° C. for 2 hours. The reaction mixture is cooled and poured onto 400 ml. of ice/water mixture. The resultant precipitate is filtered, dissolved in methylene chloride, and the methylene chloride solution is dried, filtered and evaporated to dryness, affording 4-amino-3,5-dibromobenzenesulfonylchloride, m.p. 153°–155° C.

What is claimed is:

1. A method for the treatment of mature and immature liver fluke which comprises administering to an animal susceptible to infestation with mature or immature liver fluke a fasciolicidally effective amount of a compound having the formula:

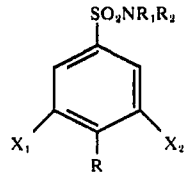

wherein R is amino; $X_1$ and $X_2$ are each halogen, trifluoromethyl or nitro; and $R_1$ and $R_2$ are each hydrogen or loweralkyl.

2. The method of claim 1 in which the compound is orally administered in an amount of from 1 to 300 mg/kg or animal body weight.

3. The method of claim 2 in which the compound is orally administered in an amount of from 10 to 100 mg/kg of animal body weight.

4. The method of claim 1 in which $X_1$ and $X_2$ are both bromine.

5. The method of claim 4 in which the compound administered is 4-amino-3,5-dibromobenzenesulfonamide.

6. The method of claim 1 in which $X_1$ and $X_2$ are both trifluoromethyl.

* * * * *